US00PP13089P2

(12) United States Plant Patent
Zary

(10) Patent No.: US PP13,089 P2
(45) Date of Patent: Oct. 15, 2002

(54) HYBRID TEA ROSE PLANT NAMED 'JACEPIRT'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/779,075

(22) Filed: Feb. 7, 2001

(65) Prior Publication Data

US 2002/0108153 P1 Aug. 8, 2002

(51) Int. Cl.[7] ..... A01H 5/00

(52) U.S. Cl. ..... Plt./132

(58) Field of Search ..... Plt./132, 130

*Primary Examiner*—Bruce R. Campell

*Assistant Examiner*—June Hwu

(74) *Attorney, Agent, or Firm*—Klarquist Sparkman, LLP

(57) ABSTRACT

Hybrid tea rose plant having large, bright pink and light yellow striped flowers having a spicy fragrance; dark green, glossy foliage and vigorous, upright growth.

1 Drawing Sheet

BOTANICAL CLASSIFICATION

*Rosa hybrida* 'JACepirt'.

The present invention relates to a new and distinct variety of rose plant of the hybrid tea class which was originated by me by crossing an unnamed seedling with an unnamed seedling.

The primary objective of this breeding was to produce a new rose variety having the bright pink and white stripes on the flowers of the hybrid tea female parent combined with the vigorous growth, large flower size and fragrance of the male parent. The objective was substantially achieved, along with other desirable improvements, as evidenced by the following unique combination of characteristics that are outstanding in the new variety and that distinguish it from its parents, as well as from all other varieties of which I am aware:

1. Bright pink and light yellow striped flowers;
2. Large flower size;
3. Vigorous, upright growth;
4. Spicy fragrance; and
5. Dark green, glossy foliage.

Asexual reproduction of this new variety by budding on Dr. Huey understock, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart (1966), except where ordinary dictionary significance of color is indicated.

Parentage:

*Seed parent.*—Unnamed. (unnamed seedling×unnamed seedling.).

*Pollen parent.*—Unnamed. (Bridal Pink×unnamed seedling.).

Classification:

*Commercial.*—Hybrid tea.

FLOWER

Observations made from specimens beginning at two years of age grown in a garden environment at Somis, Calif. from March, 1999 to November, 2000.

Blooming habit: Continuous.

Bud:

*Size.*—About 1¾ inches long when the petals start to unfurl.

*Form.*—The bud form is long, pointed ovoid.

*Color.*—When sepals first divide, bud color is Yellow Group 8C in areas along with Red Group 47B. When half blown, the upper sides of the petals are Red Group 53D with areas of Yellow Group 8D. The lower third of petal, in a broad half-moon, is Yellow Group 8C; and the lower sides of the petals are Yellow Group 8C except around the very edge of the petals where there is a faint edge of Red Group 53D.

*Sepals.*—Color: Green Group 53C with areas of Greyed-Purple Group 183C where they are exposed to bright sunlight. Surface texture: Covered in fine hairs. Length ¾ inch. Width: ⅜ inch. There are three lightly appendaged sepals. There are two unappendaged sepals with hairy edges.

*Receptacle.*—Color: Green Group 139B. Shape: Funnel. Size: Medium, about ⅜"×¼". Surface: Smooth but with many very fine hairs.

*Peduncle.*—Length: Medium, averaging about 2½ inches. Surface: Smooth. Color: Green Group 137D except where exposed to bright sunlight. Then it is Greyed-Purple Group 183A. Strength: Stiff, erect.

Bloom:

*Size.*—Large. Average open size is 4½ inches.

*Borne.*—Singly.

*Stems.*—Strength: Strong. Average length is about 14–18 inches.

*Form.*—When first open: High centered.

*Permanence.*—Flattens, petals curl back.

*Petalage.*—Number of petals under normal conditions: 25.

*Color.*—The upper sides of the petals are Red Group 53D on the outer portions with areas of Yellow Group 8D. The inner third of the petal is Yellow Group 8C. The reverse sides of the petals are Yellow Group 8C except around the petal edge where there is a thin line of Red Group 53D. The base of each petal has a small (3/16"×3/16") area of Yellow Group 13B on the upper surface. The lower surface has no discernible color spot. The major color on the upper side is Red Group 53D.

*Variegations.*—None.

*Discoloration.*—The general tonality at the end of the first day: No change. At the end of the third day: No change. By day five or six, there is a fading of the yellow coloration on upper surface to Yellow Group 8D.

*Fragrance.*—Moderate, spicy.

Petals:

*Texture.*—Thick.

*Shape.*—Round.

*Form.*—Tips slightly recurved.

*Arrangement.*—Imbricated. There are no petaloids in the center.

*Persistence.*—Petals drop off cleanly before drying.

*Lastingness.*—On the plant: Fair (about 6 days). As a cut flower: Fair (about 6 days).

Reproductive parts:

*Stamens.*—Number: 180–200. Anthers: Length: 1/16 inch. Color: Yellow-Orange Group 16C. Arrangement: Regular around styles. Filaments: Color: Yellow-Orange Group 16C, but near the base become Yellow-Orange Group 17D. Length: 3/16 inch. Stigmas: Pollen: Color: Yellow-Orange Group 22B.

*Pistils.*—Number: 140–160. Styles: Color: Red Group 53B. Length: 3/32 inch. Color: Yellow-White Group 158B. Length: 1/32 inch.

*Hips.*—Not observed with natural pollination.

Plant:

*Form.*—Bush.

*Growth.*—Vigorous, upright, branching. At maturity, height is 5½ feet, width is 4 feet.

Foliage: Number of leaflets on normal mid-stem leaves: 5 or 7.

*Size.*—Medium (5½ inches long×1½ inches wide).

*Quantity.*—Abundant.

*Color.*—New foliage: Upper and lower surfaces: Greyed-Red Group 178A. Old foliage: Upper surface: Green Group 131A. Lower surface: Green Group 139B.

Leaflets:

*Shape.*—Pointed oval. Apex shape: Acuminate. Base shape: Rounded.

*Texture.*—Leathery, glossy.

*Edge.*—Serrated.

*Serration.*—Single, small.

*Petiole rachis.*—Color: Green Group 139C.

*Petiole underside.*—Smooth with occassional prickles.

*Stipules.*—Medium (about ½ inches), serrated. Color: Green Group 139C often with a prominent vein of Yellow-Green Group 145C in the center.

*Disease resistance.*—Resistant to mildew and rust, susceptible to blackspot under normal growing conditions.

Wood:

*New wood.*—Color: Greyed-Purple Group 183A. Bark: Smooth.

*Old wood.*—Color: Green Group 137B. Bark: Smooth.

Prickles:

*Quantity.*—On main canes from base: Ordinary. On laterals from main canes: Ordinary.

*Form.*Medium, hooked downward.

*Color when young.*—Greyed-Purple Group 187A.

*Color when mature.*—Greyed-Orange Group 173C. Size: ¼ inch.

Small prickles:

*Quantity.*—On main stalks: None. On laterals: None.

Hardiness: Winter hardiness to Zone 5. Thrives in climates with day-type temperatures up to 115° F. and night temperatures not exceeding 90° F.

I claim:

1. A new and distinct variety of rose plant of the hybrid tea class, substantially as herein shown and described, characterized particularly by its large, bright pink and light yellow striped flowers having a spicy fragrance; dark green, glossy foliage and vigorous, upright growth.

* * * * *

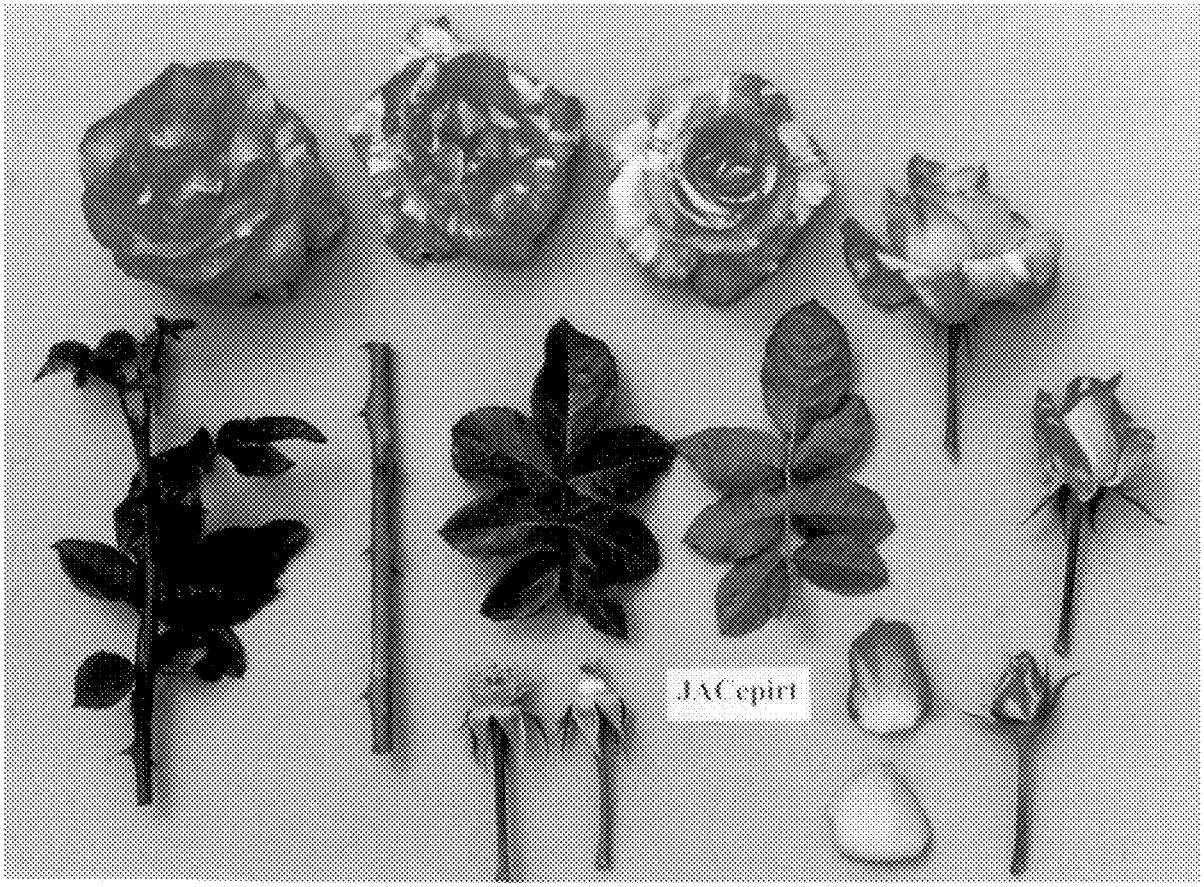
JACepirt

UNITED STATES PATENT AND TRADEMARK OFFICE

CERTIFICATE OF CORRECTION

PATENT NO. : PP 13,089 P2
DATED : October 15, 2002
INVENTOR(S) : Keith W. Zary

It is certified that error appears in the above-identified patent and that said Letters Patent is hereby corrected as shown below:

Column 3,
Line 42, delete "Stigmas:"
Line 45, after "inch." insert -- Stigmas: --

Signed and Sealed this

Twentieth Day of January, 2004

JON W. DUDAS
*Acting Director of the United States Patent and Trademark Office*